(12) United States Patent
Karell

(10) Patent No.: US 7,873,421 B2
(45) Date of Patent: Jan. 18, 2011

(54) NASAL DILATOR ADAPTED TO PROVIDE ELECTRICAL STIMULATION

(76) Inventor: Manuel L Karell, 1084 Jost Ln., Alameda, CA (US) 94502

(*) Notice: Subject to any disclaimer, the term of this patent is extended or adjusted under 35 U.S.C. 154(b) by 134 days.

(21) Appl. No.: 11/877,405

(22) Filed: Oct. 23, 2007

(65) Prior Publication Data
US 2009/0101139 A1    Apr. 23, 2009

(51) Int. Cl.
*A61N 1/18* (2006.01)
(52) U.S. Cl. .................. 607/135; 607/42; 607/118; 128/200.24; 606/199
(58) Field of Classification Search ............... 607/2, 607/42, 118, 135, 148, 48; 128/848, 858, 128/863, 203.22, 203.27, 203.29, 200.24
See application file for complete search history.

(56) References Cited

U.S. PATENT DOCUMENTS

| | | | |
|---|---|---|---|
| 0,576,441 A | 6/1891 | Farmer | |
| 1,043,924 A | 11/1912 | Goklieb | |
| 4,084,595 A | 4/1978 | Miller | |
| 4,414,977 A | 11/1983 | Rezakhany | |
| 4,989,605 A | 2/1991 | Rossen | |
| 5,476,091 A | 12/1995 | Johnson | |
| 5,533,499 A | 7/1996 | Johnson | |
| 5,665,104 A * | 9/1997 | Lee | 606/199 |
| 5,706,800 A | 1/1998 | Cronk | |
| 5,713,833 A | 2/1998 | Milligan | |
| 5,890,486 A | 4/1999 | Mitra | |
| 6,006,746 A | 12/1999 | Karell | |
| 6,238,411 B1 | 5/2001 | Thorner | |
| 6,336,456 B1 | 1/2002 | Ruben | |
| 6,961,622 B2 | 11/2005 | Gilbert | |
| 2004/0192423 A1* | 9/2004 | Nevermann | 455/575.6 |
| 2006/0000472 A1* | 1/2006 | Fenton | 128/200.24 |

* cited by examiner

*Primary Examiner*—Mark W. Bockelman
*Assistant Examiner*—Erica Lee

(57) ABSTRACT

An internal nasal dilator or an external nasal dilator is adapted to provide electrical stimulation. The user applies that nasal dilator to the nose. Within the adhesive portion is an electrode deriving energy from a neuromuscular stimulator. The electrical stimulation enhances air flow to the respiratory system. The nasal dilator may also be an internal variety and may also contain a medication delivery or heating element.

5 Claims, 3 Drawing Sheets

NASAL DILATOR ADAPTED TO PROVIDE ELECTRICAL STIMULATION

CROSS REFERENCE TO RELATED PATENTS

NOT APPLICABLE

STATEMENT REGARDING FEDERAL SPONSORED RESEARCH AND DEVELOPMENT

NOT APPLICABLE

NAMES OF PARTIES TO JOINT RESEARCH AGREEMENT

NOT APPLICABLE

BACKGROUND OF THE INVENTION

1. Field of the Invention

This invention relates generally to the field of devices for the treatment of respiratory conditions in which nasal dilation is performed. In particular, this invention relates to nasal dilators with the adaptation of providing electrical stimulation.

2. Background Description

Normal respiration requires that air passages remain open. Blockage of the nasal passages, for example from a deviated septum, or allergic swelling of tissues, may result in reduction in oxygen delivery to the brain and/or heart and may be part of the syndrome of snoring and/or obstructive sleep apnea (OSA). Nasal obstruction may lead to sustained mouth breathing and possible lung irritation.

Anatomically, the vestibule, which is immediately above the entrance to the nostril, tapers inwardly to a narrowed neck-like region called the ostium internum, above which the nasal passages widen out again. Nasal obstructions commonly occur at the ostium, wherein the lateral wall (i.e., the outer wall tissue of the nasal passage) draws in during the process of inhalation acting as a "check valve" blocking air flow.

As an alternative to surgery, internal and external nasal dilators for aiding breathing through the nose have been devised. These devices are well known in the prior art; for example, U.S. Pat. No. 576,441 to Farmer issued in 1897 is an early internal nasal expander and U.S. Pat. No. 1,043,924 to Gottlieb issued in 1912 is an early external nasal dilator. Whereas, U.S. Pat. No. 4,414,977 issued in 1983 to Rezakhany, and U.S. Pat. No. 5,533,499 issued in 1994 to Johnson are more modern concepts of nasal dilators.

A nasal dilator may contact the nasal septum, such as U.S. Pat. No. 5,713,833 to Miligan issued in 1998. Nasal dilators have been combined with medication, as in U.S. Pat. No. 5,706,800 to Cronk issued in 1997 and with heat, as in U.S. Pat. No. 5,890,486 to Mitra issued in 1998. Nasal dilators have been utilized in eyeglasses as in U.S. Pat. No. 6,006,746 to Karell in 1998 and in surgical masks as in U.S. Pat. No. 6,336,456 to Ruben in 2002.

The instant invention combines nasal dilators with electrical stimulation. Electrical stimulation without surgically implanting of an electrode is called transcutaneous electrical nerve stimulation (TENS), also called surface electrical stimulation or electro-acupuncture. A simple TENS unit is a battery operated neuromuscluar stimulator operationally connected to electrodes in contact with a body surface. An example of a TENS unit is U.S. Pat. No. 4,084,595 issued in 1978 to Miller having capability to control pulse amplitude, rate, and width. An example of a micro-miniature surface stimulator is U.S. Pat. No. 6,961,622 issued in 2005 to Gilbert is utilized for electro-acupuncture.

In Traditional Chinese Medicine, the meridians are the channels through which Chi (the body's vital Life force) flows. Traditionally, points in the human body (acupuncture points) on meridians were reached by piercing the body with needles. By stimulating with needles or electro-acupuncture or TENS, one can effect changes in the local area, as well as distal parts of the body and its organs. Stimulating the skin or mucous membranes using electrical energy, causes nervous impulses which eventually travel to the brain. TENS for pain control has been utilized in medicine for years. Stimulating certain nerves, e.g. the vagus, may treat emotional conditions such as depression or, e.g. the eigth cranial nerve for schizophrenia. Stimulation of airway muscles and nerves has been used for treatment of obstructive sleep apnea (OSA). Nerve stimulation has been utilized to open airways, and may reduce nasal congestion with trigeminal nerve stimulation. Electro-acupuncture has been utilized locally at acupuncture points e.g. Li20 and Gv26 to help reduce nasal congestion. Nasal dilators may also contact the nasal septum region wherein at least one electrode may be utilized for stimulation of this region.

The following are examples of prior art which may be useful in the understanding of the utility of the instant invention:

U.S. Pat. No. 6,238,411 to Thorner entitled "INTERNAL NASAL DILATOR" is described and the entire disclosure of which is incorporated herein by reference.

U.S. Pat. No. 6,453,901 to Ierulli entitled "NASAL DILATOR AND METHOD OF MAKING SAME" is described and the entire disclosure of which is incorporated herein by reference.

U.S. Pat. No. 7,055,523 to Brown entitled "INTERNAL NASAL DILATOR AND DELIVERY MECHANISM" is described and the entire disclosure of which is incorporated herein by reference.

U.S. Pat. No. 5,476,091 to Johnson entitled "DILATOR FOR ANATOMICAL OUTER WALL TISSUES WHICH IS ADHESIVELY MOUNTED" is described and the entire disclosure of which is incorporated herein by reference.

U.S. Pat. No. 6,080,179 to Gould entitled "RESILIENTLY RETRACTING EXTERNAL NASAL DILATOR" is described and the entire disclosure of which is incorporated herein by reference.

U.S. Pat. No. 6,244,265 to Cronk entitled "ADHESIVELY APPLIED EXTERNAL NASAL STRIPS AND DILATORS CONTAINING MEDICATIONS AND FRAGRANCES" is described and the entire disclosure of which is incorporated herein by reference.

U.S. Pat. No. 5,890,486 to Mitra entitled "THERMAL NASAL DILATOR AND METHOD FOR THE RELIEF OF . . . " is described and the entire disclosure of which is incorporated herein by reference.

U.S. Pat. No. 4,989,605 to Rossen entitled "TRANSCUTANEOUS ELECTRIC NERVE STIMULATION (TENS) DEVICE" is described and the entire disclosure of which is incorporated herein by reference.

U.S. Pat. No. 6,961,622 to Gilbert entitled "DEVICE FOR SURFACE STIMULATION OF ACUPUNCTURE POINTS" is described and the entire disclosure of which is incorporated herein by reference.

BRIEF SUMMARY OF THE INVENTION

The instant invention is the combination of a nasal dilator with a neuromuscular stimulator having electrodes for contacting tissues to enhance nasal dilation for improved breathing.

The instant invention is an internal nasal dilator apparatus adapted to comprise a neuromuscular stimulator having electrodes for contacting tissues within the nose to enhance nasal dilation.

The instant invention is an external nasal dilator apparatus adapted to comprise a neuromuscular stimulator having electrodes for contacting tissues of the nose to enhance nasal dilation.

The instant invention is a method having an internal nasal dilator adapted to comprise a neuromuscular stimulator having electrodes for contacting tissues within the nose to enhance nasal dilation.

The instant invention is a method having an external nasal dilator adapted to comprise a neuromuscular stimulator having electrodes for contacting tissues of the nose to enhance nasal dilation.

The instant invention is the combination of a nasal dilator adapted to comprise a neuromuscular stimulator having electrodes for contacting tissues to enhance nasal dilation for improved breathing utilizing acupuncture points for treatment.

The instant invention is the combination of a nasal dilator adapted to comprise a neuromuscular stimulator having electrodes for contacting tissues to enhance nasal dilation for improved breathing utilizing medication delivery elements for further enhancement.

The instant invention may also include thermal elements to enhance air flow.

These and other objects and advantages of the invention will become apparent from a reading of the following detailed specification in conjunction with the accompanying drawings.

DETAIL DESCRIPTION OF THE INVENTION

Figure 1A:
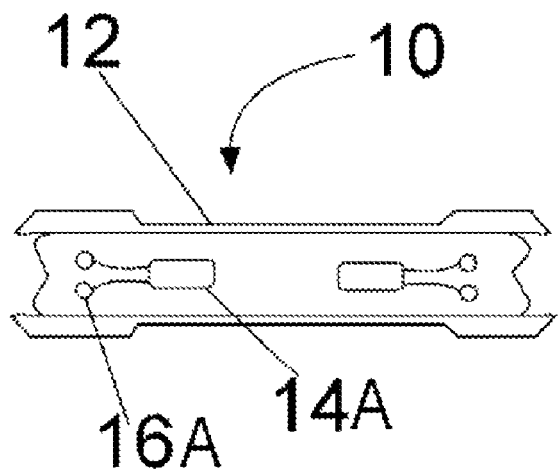
FIG. 1A and FIG. 1B are pictorial drawings of the apparatus, showing an external nasal dilator combined with a stimulator.
Figure 1B:
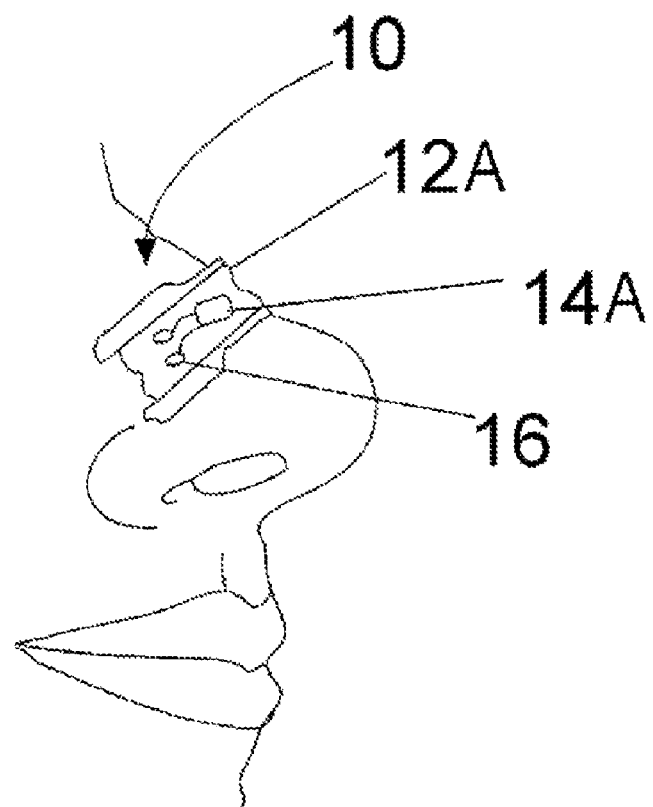

Referring to FIG. 1A the instant invention (10) generally consisting of a combination of nasal dilator with neuromuscular stimulator, in which an external nasal dilator (12) is generally flat but on application to the nose, becomes curved as is pictured in FIG. 1B to provide outward pulling pressure to the nasal wall. The instant invention (10) comprises an external nasal dilator (12) with at least one stimulator (14A) operatively attached to one or more electrodes (16A). In operation, the nasal dilator is applied and adhered to the nose. The energized electrodes coming from the stimulator enhances dilation. Various external nasal dilators and stimulators are well known in prior art and are not individually depicted.

Figure 2A:
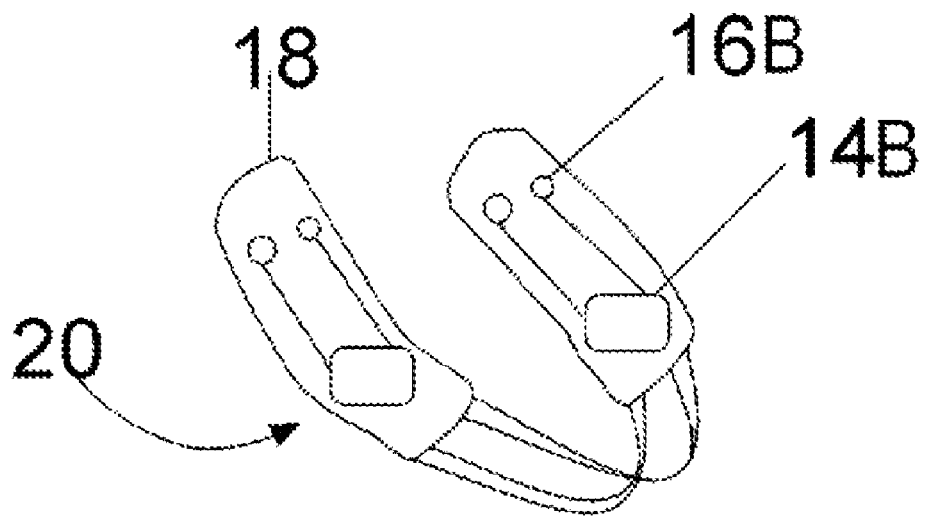
FIG. 2A and FIG. 2B are pictorial drawings of the apparatus, showing an internal nasal dilator combined with a stimulator.
Figure 2B:
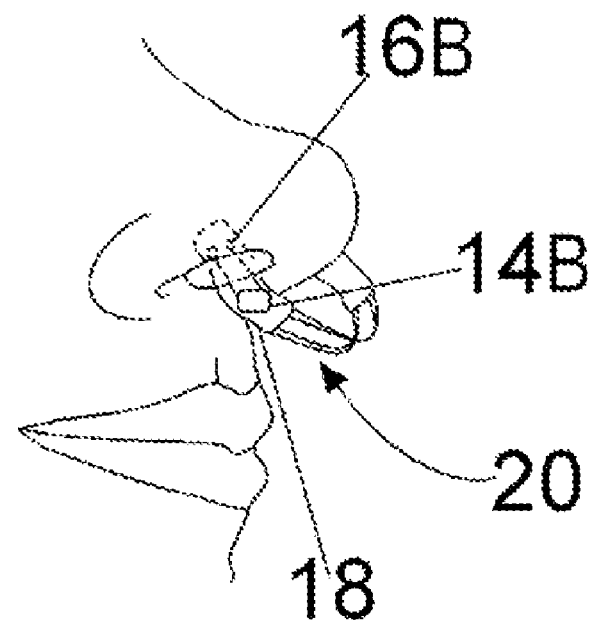

Referring to FIG. 2A, another embodiment of the instant invention (20) generally consisting of a combination of nasal dilator with neuromuscular stimulator, in which an internal nasal dilator (18) is generally under tension to extend out but on insertion into the nose, has spring energy to expand as is pictured in FIG. 2B to provide outward pushing pressure to the nasal wall. The instant invention (20) comprises an external nasal dilator (18) with at least one stimulator (14B) operatively attached to one or more electrodes (16B). In operation, the nasal dilator is inserted into the nose. The energized electrodes coming from the stimulator enhances dilation. Various internal nasal dilators and stimulators are well known in prior art and are not individually depicted.

Figure 3A:
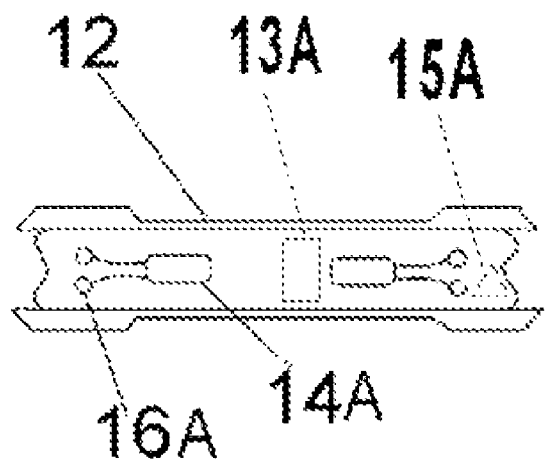
FIG. 3A and FIG. 3B are pictorial drawings showing thermal and medication elements.

Referring to FIG. 3A the instant invention additionally comprises thermal generating element 15A and medicating element 13A.

Figure 3B:
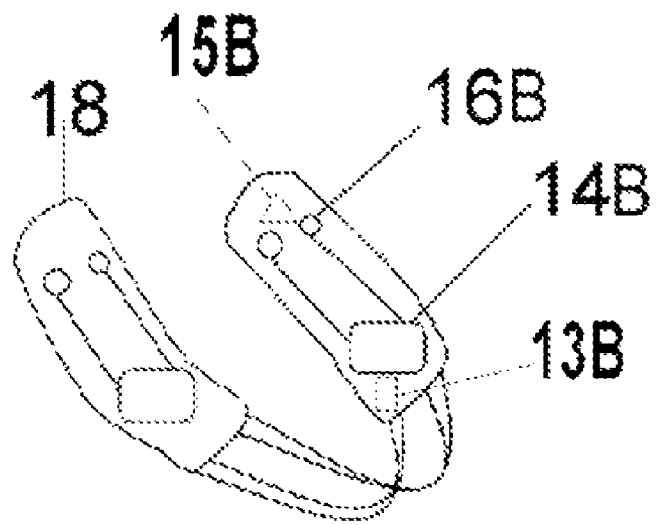

Referring to FIG. 3B the instant invention additionally comprises thermal generating element 15B and medicating element 13B.

Accordingly, it is seen that the present invention fully accomplishes its intended objects. While there has been disclosed and described in detail a preferred embodiment of the invention, it has been done by way of illustration, and not by way of limitation. It is realized that the stimulator of the present invention can assume additional forms, and it is intended to include within the scope of the appended claims all modifications and variations naturally occurring to those skilled in the art.

What is claimed is:

1. A nasal dilator apparatus adapted to provide electrical stimulation to a user comprising:
    an internal nasal dilator means or an external nasal dilator means for contacting at least one nasal cavity or nostril or nose or acupuncture point of a user for increasing air communication with the user's respiratory system; and
    at least one stimulator means for enhancing nasal dilation comprising:
        a stimulator; and
        at least one electrode means for contacting the internal nasal tissues or external nasal tissues or acupuncture points of the user for enhancing nasal dilation;
    wherein at least a portion of the at least one stimulator means is positioned on the internal nasal dilator means or external nasal dilator means.

2. A method for providing nasal dilation with electrical stimulation in an upper airway system, said method comprising:
    the step of providing an internal or an external nasal dilator for enhancing nasal dilation having at least one stimulator with one or more electrodes for contacting the user;
    the step of adhering said nasal dilator onto the nose or inserting said nasal dilator into the nose of the user and having said electrodes contact the user; and
    the step of energizing said electrodes for enhancing nasal dilation.

3. A nasal dilator apparatus adapted to provide electrical stimulation to a user comprising:
    a spreading means having a portion for adhering to at least one nostril to move at least one wall thereof outwardly for increasing the opening of a nasal passage;
    at least one stimulator means for enhancing nasal dilation comprising:
        a stimulator for providing electrical stimulation; and at least one electrode means for contacting the user operatively connected to and deriving energy from said stimulator for enhancing nasal dilation;

wherein at least a portion of the at least one stimulator means is positioned on the spreading means.

4. A nasal dilator apparatus adapted to provide electrical stimulation to a user comprising:

a spreading means having a portion for insertion in at least one nostril to move at least one wall thereof outwardly for increasing the opening of the nasal passage;

at least one stimulator means for enhancing nasal dilation comprising:

a stimulator for providing electrical stimulation; and at least one electrode means for contacting the user operatively connected to and deriving energy from said stimulator for enhancing nasal dilation;

wherein at least a portion of the at least one stimulator means is positioned on the spreading means.

5. The nasal dilator apparatus of claim 1, claim 3 or claim 4 additionally comprising a medication element means for medicating the user or a thermal element means for heating the user.

* * * * *